United States Patent [19]

Klusener et al.

[11] Patent Number: 5,258,546
[45] Date of Patent: Nov. 2, 1993

[54] CARBONYLATION CATALYST SYSTEM

[75] Inventors: Peter A. Klusener; Hans A. Stil; Fit Drent; Peter Arnoldy, all of Amsterdam, Netherlands

[73] Assignee: Shell Oil Company, Houston, Tex.

[21] Appl. No.: 979,032

[22] Filed: Nov. 20, 1992

Related U.S. Application Data

[62] Division of Ser. No. 868,394, Apr. 14, 1992, Pat. No. 5,189,003.

[30] Foreign Application Priority Data

May 30, 1991 [GB] United Kingdom ............... 91115832

[51] Int. Cl.$^5$ ............................................. C07C 67/36
[52] U.S. Cl. .................................... 560/207; 562/522; 554/129; 560/97; 560/114; 560/232
[58] Field of Search ................. 560/207, 97, 114, 232; 562/522; 554/129

[56] References Cited

U.S. PATENT DOCUMENTS

| | | |
|---|---|---|
| 4,824,817 | 4/1989 | Drent . |
| 5,028,576 | 7/1991 | Drent et al. . |
| 5,158,921 | 10/1992 | Drent et al. .......................... 560/207 |
| 5,166,411 | 11/1992 | Drent ................... 560/522 |
| 5,177,253 | 1/1993 | Drent ................... 560/522 |
| 5,179,225 | 1/1993 | Drent et al. .......................... 560/207 |

FOREIGN PATENT DOCUMENTS

| | | |
|---|---|---|
| 186228 | 2/1986 | European Pat. Off. . |
| 203286 | 12/1986 | European Pat. Off. . |
| 218970 | 4/1987 | European Pat. Off. . |
| 283616 | 9/1988 | European Pat. Off. . |
| 305012 | 3/1989 | European Pat. Off. . |
| 441447 | 8/1991 | European Pat. Off. . |

Primary Examiner—Paul J. Killos

[57] ABSTRACT

The invention relates to a catalyst system, which comprises a source of a Group VIII metal and a polyphosphine. The invention further relates to a process for the preparation of alpha, beta-olefinically unsaturated compounds utilizing this catalyst system.

3 Claims, No Drawings

CARBONYLATION CATALYST SYSTEM

This is a division, of application Ser. No. 868,394, filed Apr. 14, 1992, now U.S. Pat. No. 5,189,003.

FIELD OF THE INVENTION

This invention relates to a novel catalyst system comprising a polyphosphine, to certain novel polyphosphines, and to the use of the catalyst system in the carbonylation of ethylenically or acetylenically unsaturated compounds.

BACKGROUND OF THE INVENTION

Many processes are known in the art for the carbonylation of olefinically or acetylenically unsaturated compounds. A review of such processes is provided by J. Falbe, "New Syntheses with Carbon Monoxide", Springer-Verlag, Berlin Heidelberg New York, 1980. Typically, the processes involve the reaction of an olefinically or acetylenically unsaturated compound with carbon monoxide and, in some cases, hydrogen or a nucleophilic compound having a removable hydrogen atom, in the presence of a carbonylation catalyst system. In many instances, the carbonylation catalyst system comprises a source of a Group VIII metal and a ligand such as a phosphine.

One type of catalyst system which has been disclosed in recent years comprises a source of a Group VIII metal and a pyridyl phosphine.

Kurti Kurtev et al, Journal of the Chemical Society, Dalton Transactions, 1980, pages 55 to 58 disclose catalyst systems comprising a rhodium or ruthenium compound and a pyridyl phosphine, and their use in the carbonylation of hex-1-ene.

European Patent No. A1-0259914 discloses catalyst systems comprising a palladium compound, a pyridyl phosphine, an acid and a quinone and their use in the carbonylation of olefins to afford polymers.

European Patent No. A1-0271144 discloses the use of catalyst systems comprising a palladium compound, a pyridyl phosphine and an acid in the carbonylation of acetylenes with hydroxyl-containing compounds.

European Patent No. A1-0282142 discloses the use of catalyst systems comprising a palladium compound, a pyridyl phosphine and an acid in the carbonylation of olefins with hydroxyl-containing compounds.

European Patent No. A1-0386833 discloses catalyst systems comprising a palladium compound and a (substituted-2-pyridyl) phosphine. As suitable substituents, hydroxyl, amino, amido, cyano, acyl, acyloxy, hydrocarbyl and hydrocarbyloxy groups; and halogen atoms are mentioned.

None of the aforementioned references describes experiments in which a catalyst system comprising a polyphosphino-substituted N-heteroaryl compound is used.

Newkome et al, J. Org. Chem., 43, 947 (1978), disclose the preparation of 2,6-bis(diphenylphosphino) pyridine.

It has now been found that carbonylation reactions can proceed at an extremely high rate using a catalyst system comprising certain polyphosphino-substituted N-heteroaryl compounds, particularly at a low ratio of the phosphine ligand to the catalyst metal component. Moreover, beta-carbonylated products may be obtained with remarkably high selectivity when an alpha-unsaturated hydrocarbon, in particular propyne, is carbonylated using such catalyst systems.

SUMMARY OF THE INVENTION

The present invention therfore provides a catalyst system, which comprises
a) a source of a Group VIII metal, and
b) a polyphosphine of general formula:

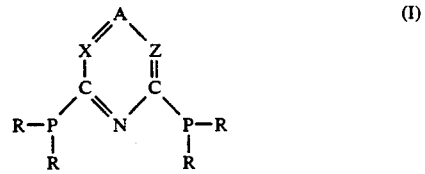

in which
each R is independently selected from an alkyl, cycloalkyl, aryl or heteroaryl group; and
each of A, X and Z is independently selected from a nitrogen atom, a CH group, a group of formula C-PR$_2$ with R being defined as hereinbefore, and a group of formula CR', wherein R' represents a hydroxyl group, an amino group, an amido group, a cyano group, an acyl group, an acyloxy group, a halogen atom, a hydrocarbyl group, a heteroaryl group or a hydrocarbyloxy group, it also being possible for two adjacent CR' groups to form a ring; or an acid addition salt thereof.

DESCRIPTION OF THE PREFERRED EMBODIMENTS

Catalyst systems comprising a source of a Group VIII metal and a polyphosphine of general formula (I), or a salt thereof, have been found to allow the carbonylation of alpha-unsaturated hydrocarbons such as propyne to proceed at a rate as high as 100,000 moles of converted propyne per gram atom of palladium per hour at a reaction temperature of 45° C. Moreover, excellent conversion rates could be obtained using a catalyst system having a relatively low ratio between the polyphosphine and palladium. Besides, the present catalyst system has been found to afford beta-carbonylated products from alpha-unsaturated hydrocarbons, such as propyne with very high selectivity of 99.9% and above.

Without wishing to be bound by theory, it is believed that sterical constraint due to the N-aromatic six-membered ring, precludes the polyphosphine of general formula (I) from coordinating to a single Group VIII metal atom in a P,P-bidentate mode. Accordingly, it is surprising that the present catalyst systems are effective when comprising lower ratios of phosphine ligand to palladium as compared with other monodentate phosphine ligands. It is further believed that the second phosphino group exerts a steric effect during the carbonylation of alpha-unsaturated compounds, thereby favoring the formation of beta-carbonylated products.

Polyphosphines of the general formula (I) may be thought of as being derived from an N-aromatic six-membered ring having at least one nitrogen ring atom adjacent to two carbon atoms each carrying a phosphino substituent. Examples of N-aromatics constituting a suitable ring core for the polyphosphines of general formula (I), include pyridine, pyrimidine, pyrazine, isoquinoline, 1,3,5-triazine, 1,2,4-triazine, and quinazoline.

A preferred example is pyridine, i.e. in formula (I), each of X, Z, and A is independently selected from a CH group and a group of formula CR'. Further preferred examples include pyrimidine and 1,3,5-triazine, especially when being substituted with three phosphino groups at the 2-, 4-, and 6-positions, i.e. in formula (I), at least one of X and Z is nitrogen, and A is a group C-PR$_2$.

When reference is made in this specification to a particular group, it is understood that the group may be either unsubstituted or it may be substituted with one or more, for example one, two or three, substituents selected from the group consisting of a halogen atom, an alkyl group, an aryl, a haloalkyl group, an alkoxy group and a haloalkoxy group.

As used herein, the term "an amino group" is used to refer to the group NH$_2$or an alkyl or dialkylamino group.

As used herein, the term "an acyl group" is used to refer to an alkanoyl group such as, for example, acetyl.

As used herein, the term "an amido group" is used to refer to an acylamino group such as, for example, acetamido.

A ring formed by two adjacent CR' groups is preferably a hydrocarbyl ring, for example a phenyl ring. It is understood that the hydrocarbyl ring may be substituted with any substituent which does not interfere with the reaction. Examples of N-aromatics having two adjacent CR' groups which form a ring are isoquinoline and quinazoline.

When reference is made to a hydrocarbyl or hydrocarbyloxy group, the hydrocarbyl moiety preferably represents an alkyl group, a cycloalkyl group or a phenyl group.

As used herein, an alkyl group refers to groups having up to 20 carbon atoms, more preferably up to 12 carbon atoms, especially from 1 to 4 carbon atoms. For example, the alkyl group may be a methyl, ethyl, n-propyl, iso-propyl, n-butyl, iso-butyl or tert-butyl group.

As used herein, a cycloalkyl group refers to groups having from 3 to 6 carbon atoms.

As used herein, the term "halogen atom" refers to fluorine, chlorine or bromine atoms.

As used herein, an "aryl group" refers to a phenyl or naphthyl group.

A heteroaryl group may be derived from any of the aforementioned N-aromatics, but may also comprise other hetero atoms such as oxygen, and/or be a five- or seven-membered ring.

A heteroaryl group may specifically be a radical derived from a compound of above general fomula (I) by abstraction of a hydrogen atom from any CH group represented by A, X, or Z. When such a heteroaryl group is represented by R, the above formula (I) represents oligomeric compounds comprising chains of repeating phosphino pyridyl moieties interconnected by bridging phosphino groups, as in bis[6-(diphenylphosphino) 2-pyridyl] phenyl phosphine or 2,6-bis{[6-(diphenylphosphino) 2-pyridyl] phenyl phosphino} pyridine. When such a heteroaryl group is represented by R', the above formula (I) represents biheteroaryl compounds carrying at least four phosphino substituents, as in 4,4'-bi[2,6-bis(diphenylphosphino) pyridyl].

Preferably, each group R' is independently selected from a halogen atom, a C$_{1-4}$ alkyl group and a C$_{1-4}$ alkoxy group. More preferably, each group R' represents a C$_{1-4}$ alkyl group.

Preferably, each group R of the phosphino substituents independently represents a phenyl group.

Most preferably, the polyphosphine of general formula (I) is a 2,6-bis(dihydrocarbylphosphino) pyridine, especially a 2,6-bis(diarylphosphino) pyridine.

Examples of polyphosphines of general formula (I) include 2,6-bis(diphenylphosphino) pyridine, 2,6-bis(di-p-tolylphosphino) pyridine, 2,6-bis(methylphenylphosphino) pyridine, 2,6-bis(dicyclohexylphosphino) pyridine, 2,6-bis(di-p-methoxyphenylphosphino) pyridine, 3,4'-bi[2,6-bis(diphenyl phosphino) pyridyl ], 2,6-bis(diphenylphosphino) pyrazine, 2,2'-bi[3,5-bis(diphenylphosphino) pyrazine], 1,3-bis(diphenylphosphino) isoquinoline, 2,4-bis(diphenylphosphino) 1,3,5-triazine, 2,4,6-tris(diphenylphosphino) 1,3,5-triazine, 2-chloro 4,6-bis(diphenylphosphino) 1,3,5-triazine, 1,3-bis(diphenylphosphino) quinazoline, 2,4-bis(diphenylphosphino) pyrimidine, and 2,4,6-tris(diphenylphosphino) pyrimidine.

Preferred acid addition salts of the polyphosphines of general formula (I) include salts with sulfuric acid; a sulfonic acid, e.g. a hydrocarbylsulfonic acid such as an arylsulfonic acid, e.g. benzenesulfonic acid, p-toluenesulfonic acid or naphthalenesulfonic acid, an alkylsulfonic acid, e.g. methanesulfonic acid or t-butylsulfonic acid, or an alkyl sulfonic acid such as 2-hydroxypropanesulfonic acid, trifluoromethanesulfonic acid, chlorosulfonic acid or fluorosulfonic acid; a phosphonic acid, e.g. orthophosphonic acid, pyrophosphonic acid or benzenephosphonic acid; a carboxylic acid, e.g. chloroacetic acid, dichloroacetic acid, trichloroacetic acid, trifluoroacetic acid, oxalic acid or terephthalic acid; or a perhalic acid such as perchloric acid.

Examples of suitable Group VIII metals are iron, cobalt, nickel, ruthenium, rhodium, palladium, iridium, and platinum and mixtures thereof.

The catalyst system according to the invention preferably comprises a source of palladium.

The source of Group VIII metal may be, for example, the metallic element or a compound of the Group VIII metal. The source of a Group VIII metal is preferably a compound of the Group VIII metal, more preferably a compound of palladium.

Examples of compounds of Group VIII metals include salts such as, for example, salts of nitric acid; sulfuric acid; carboxylic acids such as alkane carboxylic acids having not more than 12 carbon atoms, e.g. acetic acid; and hydrohalic acids. Other examples of salts are salts of the acids mentioned above in relation to the formation of acid addition salts by the polyphosphines of general formula (I). Since halide ions can be corrosive, salts of hydrohalic acids are not preferred. Other examples of compounds of Group VIII metals include complexes, such as complexes with beta-carbonyl enolates (e.g. acetylacetonate), phosphines (e.g. a phosphine of general formula I) and/or carbon monoxide. For example the compound of a Group VIII metal may be palladium acetylacetonate, tetrakis-triphenylphosphinepalladium, bis-tri-o-tolylphosphinepalladium acetate, bis-diphenyl-2-pyridylphosphinepalladium acetate, tetrakis-diphenyl-2-pyridylphosphinepalladium, bis-di-o-tolylpyridylphosphinepalladium acetate or bis-diphenylpyridylphosphinepalladium sulfate.

The number of moles of polyphosphine of general formula (I) per gram atom of Group VIII metal in the catalyst system according to the invention is not critical. It will depend upon the particular source of Group VIII metal and the particular reactants to be carbonylated. Conveniently, the ratio of the number of moles of polyphosphine of general formula (I) per gram atom of Group VIII metal is in the range of from about 1 to about 50. A ratio in the range of from about 2 to about 20 is particularly preferred in providing very high carbonylation rates at economic use of the polyphosphine ligand. As the polyphosphine is believed to coordinate as a P-monodentate ligand, these ratios refer to the number of moles of the compounds of general formula (I) whether comprising two or more phosphino groups. Of course, compounds of formula (I) comprising a plurality of phosphino-substituted N-aromatic moieties in case R and/or R' represents a heteroaryl group having formula (I) as indicated above, may coordinate to a plurality of Group VIII metal atoms, and accordingly can be used at a lower ligand to metal ratio.

In a preferred embodiment, the catalyst system according to the invention further comprises a protonic acid. The function of the protonic acid is to provide a source of protons. The protonic acid may also provide a source of anions for the palladium complex catalytically active in, for example, the carbonylation of propyne, which complex is believed to be of a cationic nature. Preferred anions are weakly or non-coordinating to the palladium cation, and accordingly preferably derived from a protonic acid having a pKa below 2 (as measured in water at 18° C.). The protonic acid may be added as such, or be generated in situ, for example, by interaction of a Lewis acid such as $BF_3$, $AsF_5$, $SbF_5$, $PF_5$, $TaF_5$ or $NbF_5$ with a Broensted acid such as, for example, a hydrohalogenic acid, water or an alkanol such as methanol, being one of the reactants in the preparation of methyl methacrylate. Preferably, the protonic acid is one of those referred to hereinabove in relation to the formation of acid addition salts by the polyphosphines of general formula (I). The protonic acid may also be, for example, an acidic ion exchange resin, for example a sulfonated ion exchange resin, or a boric acid derivative such as $H[B(O_2C_6H_4)_2]$ or $H[B(OC_6H_4CO_2)_2]$.

It will be appreciated that a catalyst system comprising an acid addition salt of a polyphosphine of general formula (I), inevitably comprises a protonic acid.

When the catalyst system comprises a protonic acid, the ratio of the number of equivalents of protonic acid per equivalent of polyphosphine of general formula (I) may vary over a wide range. The optimal ratio of protonic acid to polyphosphine of general formula (I) will depend upon the particular reaction in which the catalyst composition is to be used. Conveniently, the number of equivalents of protonic acid per equivalent of polyphosphine of general formula (I) will be in the range of from about 0.1 to about 50, preferably from about 0.5 to about 5.

The catalyst system according to the invention is conveniently constituted in a liquid phase. The liquid phase may be formed by one or more of the reactants with which the catalyst system is to be used. Alternatively, it may be formed by a solvent. It may also be formed by one of the components of the catalyst system. The catalyst system according to the invention may be homogeneous or heterogeneous. Most preferably it is homogeneous.

The catalyst system according to the invention may be generated by any suitable method. For example, it may be prepared by combining a Group VIII metal compound, a polyphosphine of general formula (I) and, if appropriate, a protonic acid, in a liquid phase. Alternatively, it may also be prepared by combining a Group VIII metal compound and an acid addition salt of general formula (I) in a liquid phase. It may also be prepared by combining a Group VIII metal compound which is a complex of a Group VIII metal with a polyphosphine of general formula (I), and if appropriate, a protonic acid, in a liquid phase.

The polyphosphines of general formula (I) may be prepared by a process which comprises reacting a compound of the general formula:

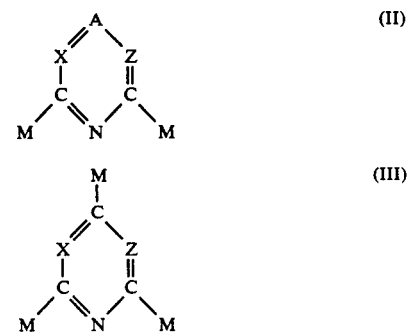

in which M represents either a metal atom or a leaving atom or group, with two or three equivalents of an appropriate compound of general formula M'-PRR (IV), in which M' represents either a leaving atom or group, or a metal atom, optionally followed by forming an acid addition salt. It will be appreciated that when M represents a metal atom, the appropriate compound of general formula (IV) is one wherein M' represents a leaving atom or group. Similarly, when M represents a leaving atom or group, the appropriate compound of formula (IV) is one wherein M' represents a metal atom. The reaction between the compound of formula (II) or (III) and the compound of formula (IV) may conveniently be effected in the presence of a solvent such as liquid ammonia, a hydrocarbon, or an ether at a temperature in the range of from about −80° C. to about 100° C.

As has been stated above, it has been found that compositions according to the invention are highly selective in the carbonylation of unsaturated hydrocarbons.

Accordingly, the invention further provides the use of a catalyst composition as defined hereinbefore in the carbonylation of an acetylenically or olefinically unsaturated hydrocarbon.

In another aspect, the invention provides a process for the carbonylation of an acetylenically or olefinically unsaturated compound, which comprises reacting an acetylenically or olefinically unsaturated compound in a liquid phase with carbon monoxide in the presence of a catalyst system as defined above.

An olefinically unsaturated compound is preferably a substituted or unsubstituted alkene or cycloalkene having from 2 to 30, preferably from 3 to 20 carbon atoms per molecule.

An acetylenically unsaturated compound is preferably a substituted or unsubstituted alkyne having from 2 to 20, especially from 2 to 10 carbon atoms per molecule.

The acetylenically or olefinically unsaturated compound may contain one or more acetylenic or olefinic bonds, for example one, two or three acetylenic or olefinic bonds.

An olefin or acetylene may be substituted with, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols, for example 3-butyn-1-ol, 4-pentyn-1-ol or 3-pentyn-1-ol. Thus 3-butyn-1-ol may be converted into alpha-methylene-gammabutyrolactone.

Examples of suitable alkynes include: ethyne, propyne, phenylacetylene, 1-butyne, 2-butyne, 1-pentyne, 1-hexyne, 1-heptyne, 1-octyne, 2-octyne, 4-octyne, 1,7-octadiyne, 5-methyl-3-heptyne, 4-propyl-2-pentyne, 1-nonyne, benzylethyne and cyclohexylethyne.

Examples of suitable alkenes include: ethene, propene, phenylethene, 1-butene, 2-butene, 1-pentene, 1-hexene, 1-heptene, I-octene, 2-octene, 4-octene, cyclohexene and norbornadiene.

The unsaturated compound may be carbonylated alone or in the presence of other reactants, for example, hydrogen or a nucleophilic compound having a removable hydrogen atom. An example of a nucleophilic compound having a removable hydrogen atom is a hydroxyl-containing compound. The hydroxyl-containing compound is preferably an alcohol, water or a carboxylic acid.

The alcohol used may be aliphatic, cycloaliphatic or aromatic and may carry one or more substituents. The alcohol preferably comprises up to about 20 carbon atoms per molecule. It may be, for example, an alkanol, a cycloalkanol or a phenol. One or more hydroxyl groups may be present, in which case several products may be formed, depending on the molar ratio of the reactants used. Examples of alkanols include methanol, ethanol, 1-propanol, 2-propanol, 1-butanol, 2-butanol, 2-methylpropan-1-ol, and 2-methylpropan-2-ol.

The process according to the present invention can be carried out using a wide variety of carboxylic acids. For example, the carboxylic acids may be aliphatic, cycloaliphatic or aromatic and may carry one or more substituents, such as those named in connection with the acetylenically and olefinically unsaturated compounds. Carboxylic acids preferably used in the process according to the invention include those containing up to 20 carbon atoms, such as formic acid, acetic acid, propionic acid, benzoic acid or adipic acid.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

It has been found that catalyst compositions according to the invention are particularly useful for the carbonylation of alpha acetylenes with hydroxyl-containing compounds.

Accordingly, to a preferred aspect, therefore, the invention provides a process for the preparation of an alpha,beta-olefinically unsaturated compound, which comprises reacting an alpha acetylene with carbon monoxide and a hydroxyl-containing compound in the liquid phase in the presence of a carbonylation catalyst as hereinbefore described.

In the process, the carbonylation catalyst is preferably a palladium catalyst as described above, namely a catalyst which comprises:
 a) a palladium compound,
 b) a polyphosphine of general formula (I), and
 c) a protonic acid.

It is not essential to use a separate solvent in the process according to the invention.

A large excess of the product or of one of the reactants, for example an alcohol, can often form a suitable liquid phase. In some cases, however, it may be desirable to use a separate solvent. Any inert solvent can be used for that purpose. Said solvent may, for example, comprise sulphoxides, sulphones, aromatic hydrocarbons, esters, ketones, ethers and amides.

The process according to the present invention is conveniently effected at a temperature in the range of from about 10° C. to about 200° C., in particular from about 20° C. to about 130° C., more preferably from about 25° C. to about 80° C.

The process according to the invention is preferably effected at a pressure of from about 1 bar to about 70 bar. Pressures higher than about 100 bar may be used, but are generally economically unattractive on account of special apparatus requirements.

The molar ratio of the hydroxyl-containing compound to the unsaturated hydrocarbon may vary between wide limits and generally lies within the range of about 0.01:1 to about 100:1.

The quantity of the Group VIII metal is not critical. Preferably, quantities are used within the range of about $10^{-7}$ to about $10^{-1}$ gram atom Group VIII metal per mol of unsaturated compound.

The carbon monoxide required for the process according to the present invention may be used in a practically pure form or diluted with an inert gas, such as, for example, nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than about 5 vol %.

The selectivity towards alpha,beta-olefinically unsaturated compounds, expressed as a percentage, is defined as $$(a/b) \times 100$$

wherein "a" is the quantity of acetylenically unsaturated compound converted into alpha,beta-olefinically unsaturated compound and "b" is the total quantity of acetylenically unsaturated compound that has been converted.

The invention will now be described by the following examples which are included for illustrative purposes and are not to be construed as limiting the invention.

ILLUSTRATIVE EMBODIMENTS

Unless otherwise stated, the allene content of any propyne used in the following examples was less than 50 ppm.

Preparation of 2,6-bis(diphenylphosphino) pyridine

To an effectively stirred solution of 13.1 g of triphenylphosphine (50 mmol) in 150 ml of dry THF (tetrahydrofuran) under an argon atmosphere was added 0.75 g of lithium metal (107 mmol). When the reaction was complete after 2 hours, as established by $^{31}$P NMR, the excess lithium was removed. Subsequently, the dark brown solution was cooled to 0° C. Thereupon, an amount of 3.4 g of tert-butanol (45.8 mmol) equivalent to the phenyl lithium present, was added, whereby the temperature increased to about 15° C. Subsequently, 3.52 g of 2,6-dichloropyridine (23.8 mmol) was added, and the temperature was allowed to rise. The mixture obtained was worked up by distillation of THF at reflux and atmospheric pressure, vacuum drying, addition of 50 ml of 3M aqueous ammonium chloride solution and 50 ml of dichloromethane, phase separation, washing, filtration of the combined organic phases, vacuum concentration, and recrystallization from boiling hexane. After cooling to ambient temperature 7.8 g of white crystalline 2,6-bis(diphenylphosphino) pyridine (yield 73.4%, purity 97.5%) was collected by filtration.

EXAMPLE 1

A 250 ml magnetically stirred stainless steel autoclave was successively filled with 0.025 mmol palladium(II) acetate, 1 mmol 2,6-bis(diphenylphosphino) pyridine, 1 mmol methanesulfonic acid, and 50 ml methanol. Air was evacuated from the autoclave, whereupon 30 ml propyne was added. Subsequently, carbon monoxide was added to a pressure of 60 bar. The autoclave was sealed and an exotherm was observed heating the reaction mixture to an average temperature of 45° C. over the reaction period. After completion of the reaction by depletion of propyne, a specimen of the contents was analysed by means of gas liquid chromatography. The selectivity of the conversion of propyne to methyl methacrylate was found to be 99.92 % while the mean conversion rate was calculated to be above 100,000 mol propyne per gram atom palladium per hour.

EXAMPLE 2

The experiment as described in Example 1 was repeated in substantially the same manner with a catalyst system composed of 0.025 mmol palladium(II) acetate, 0.25 mmol 2,6-bis(diphenylphosphino) pyridine, and 0.25 mmol methanesulfonic acid. Upon sealing of the autoclave, an exotherm raising the temperature to an average of 50° C. was observed. After a reaction time of 0.25 hour, analysis of a specimen of the contents showed a selectivity of the conversion of propyne to methyl methacrylate of 99.92%. A mean conversion rate of 50,000 mol/gram atom Pd/hour was calculated.

EXAMPLES 3 AND 4 and COMPARATIVE EXAMPLES A AND B

The method of Example 2 was repeated using 2,6-bis(diphenylphosphino) pyridine (2,6-PNP) and, for comparison, 2-diphenylphosphino pyridine (2-PN), respectively, as ligand for the catalyst system in the amounts indicated and using a reaction temperature of 22° C. The conversion rate was calculated from the change of CO pressure over the first 3 hours of the reaction, and the selectivities were obtained by GLC analysis. The results are summarized in Table 1.

By comparing Example 4 with Comparative Example A, it is seen that a ten times higher conversion rate is achievable using the polyphosphine ligand in accordance with the invention at a molar ratio of ligand to palladium of 10:1. From Example 3, it will be appreciated that the 2,6-PNP to palladium ratio could be lowered to 5:1 with still good propyne conversion rates. Comparative Example B shows that under the present carbonylation conditions, the use of 20 moles of 2-PN per gram atom of palladium per hour resulted in a conversion rate unfavorably comparing with the results for the ligand according to the invention.

TABLE 1

Carbonylation of Propyne and Methanol into Methyl methacrylate

| Example | Ligand (mmol) | Acid (mmol) | Selectivity (%) | Mean Conversion Rate (mol propyne/ gram atomPd/hour) |
|---|---|---|---|---|
| 3 | 2,6-PNP (0.125) | $CH_3SO_3H$ (0.125) | 99.92 | 3,000 |
| 4 | 2,6-PNP (0.25) | $CH_3SO_3H$ (0.25) | 99.92 | 5,000 |
| Comp. A | 2-PN (0.25) | $CH_3SO_3H$ (0.25) | 99.3 | >500 |
| Comp. B | 2-PN (0.5) | $CH_3SO_3H$ (0.25) | 99.4 | 1,000 |

Note: 0.025 mmol Pd(OAc)$_2$, 30 ml propyne, 50 ml methanol, 60 bar CO, 22° C.

EXAMPLE 5

The method of Example 3 was repeated using a catalyst system composed of 0.025 mmol palladium(II) acetate, 0.25 mmol 2,6-bis(diphenylphosphino) pyridine, and 1 mmol BF$_3$.Et$_2$O, from which the protonic acid H$^+$BF$_3$(CH$_3$O)$^-$ is formed in situ by reaction with methanol. Upon a reaction time of 3 hours at 25° C., a propyne conversion rate of 2700 mol/gat Pd/hour, and a selectivity to methyl methacrylate of 99.2% were observed.

EXAMPLE 6

A 250 ml magnetically stirred stainless steel autoclave was successively filled with 0.025 mmol palladium(II) acetate, 0.25 mmol 2,6-bis(diphenylphosphino) pyridine, 0.25 mmol methanesulfonic acid, 30 ml phenylethyne and 30 ml methanol. Air was evacuated from the autoclave, whereupon carbon monoxide was added to a pressure of 60 bar. The autoclave was sealed and an exotherm was observed heating the reaction mixture to an average temperature of 32° C. over the reaction period. After a reaction time of 0.5 hour, a specimen of the contents was analysed by means of gas liquid chromatography. The selectivity of the conversion of propyne to methyl 1-phenylacrylate was found to be 99.93 % while the mean conversion rate was calculated to be 20,000 mol propyne per gram atom palladium per hour.

What is claimed is:

1. A process for the preparation of an alpha,beta-olefinically unsaturated compound, which comprises reacting an alpha acetylene with carbon monoxide and a hydroxyl-containing compound in the presence of a carbonylation catalyst system which comprises:

a) a source of a Group VIII metal, and
 b) a polyphosphine of general formula:

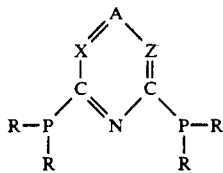 (I)

wherein
R is independently selected from an alkyl, cycloalkyl, aryl or heteroaryl group; and
each of A, X and Z is independently selected from a nitrogen atom, a CH group, a group of formula C-PR$_2$ with R being defined as hereinbefore, and a group of formula CR', wherein R' represents a hydroxyl group, an amino group, an amido group, a cyano group, an acyl group, an acyloxy group, a halogen atom, a hydrocarbyl group, a heteroaryl group or a hydrocarbyloxy group, or wherein two adjacent CR' groups to form a ring; or an acid addition salt thereof.

2. The process as claimed in claim 1, wherein the carbonylation catalyst system comprises:
a) a palladium compound,
b) a polyphosphine of general formula I, and
c) a protonic acid.

3. The process as claimed in claim 1, wherein methyl methacrylate is prepared by reacting propyne with carbon monoxide and methanol.

* * * * *